(12) United States Patent
Evans, Jr.

(10) Patent No.: US 8,353,866 B2
(45) Date of Patent: Jan. 15, 2013

(54) MULTI-CHAMBERED MIXING SYRINGE DEVICE AND METHODS OF USE

(75) Inventor: Richard T. Evans, Jr., Montclair, NJ (US)

(73) Assignee: Thomasevans, LLC, Montclair, NJ (US)

( * ) Notice: Subject to any disclaimer, the term of this patent is extended or adjusted under 35 U.S.C. 154(b) by 11 days.

(21) Appl. No.: 12/555,554

(22) Filed: Sep. 8, 2009

(65) Prior Publication Data

US 2010/0063474 A1    Mar. 11, 2010

Related U.S. Application Data

(63) Continuation of application No. PCT/US2009/056172, filed on Sep. 8, 2009.

(60) Provisional application No. 61/177,113, filed on May 11, 2009, provisional application No. 61/165,446, filed on Mar. 31, 2009, provisional application No. 61/095,867, filed on Sep. 10, 2008.

(51) Int. Cl.
    *A61M 37/00* (2006.01)
(52) U.S. Cl. .............. 604/87; 604/518; 604/82; 604/88; 604/191; 604/218; 604/232
(58) Field of Classification Search ................. 604/518, 604/82, 89, 90, 91, 191, 218, 232, 236, 87, 604/88
See application file for complete search history.

(56) References Cited

U.S. PATENT DOCUMENTS

| | | | |
|---|---|---|---|
| 2,168,686 A | 8/1939 | Saffir | |
| 2,869,543 A | 1/1959 | Ratcliff et al. | |
| 3,255,752 A | 6/1966 | Dick | |
| 3,348,546 A | 10/1967 | Roberts et al. | |
| 3,838,689 A | 10/1974 | Cohen | |
| 4,811,549 A | 3/1989 | Usami et al. | |
| 4,915,695 A | 4/1990 | Koobs | |
| 5,429,603 A | 7/1995 | Morris | |
| 5,501,371 A | 3/1996 | Schwartz-Feldman | |
| 5,876,372 A | 3/1999 | Grabenkort et al. | |
| 6,612,465 B2 | 9/2003 | Pierson et al. | |
| 7,018,089 B2 | 3/2006 | Wenz et al. | |
| 2002/0052579 A1 | 5/2002 | Sogaro | |

FOREIGN PATENT DOCUMENTS

| | | |
|---|---|---|
| EP | 0 695 555 A1 | 2/1996 |
| EP | 1 205 196 A1 | 5/2002 |
| GB | 2 443 799 A | 5/2008 |

OTHER PUBLICATIONS

International Search Report mailed on Dec. 21, 2009 in Application No. PCT/US2009/056172, 10 pages.

*Primary Examiner* — Bhisma Mehta
(74) *Attorney, Agent, or Firm* — Dorsey & Whitney LLP (57) ABSTRACT

The present invention relates to a mixing syringe device for delivering a medicament or medical composition to a site of interest. The mixing syringe device generally includes a multi-chambered open lumen and optionally a sectioned plunger. The open lumen has at least two longitudinally oriented chambers within the interior of the lumen, and the optional sectioned plunger has at least two longitudinally oriented extensions corresponding in configuration to the at least two longitudinally oriented chambers of the open lumen and configured to be reciprocatably disposed in the chambers of the open lumen. Each compartment of the lumen is configured to store a medicament component or medical composition component in its interior. In certain embodiments, each compartment is sealed at one end by a movable stopper mechanism and sealed at the other end by a sealing mechanism capable of temporarily or otherwise opening. Methods of use are also provided.

5 Claims, 8 Drawing Sheets

FIG. 6E

MULTI-CHAMBERED MIXING SYRINGE DEVICE AND METHODS OF USE

CROSS REFERENCE TO RELATED APPLICATIONS

The present invention is related to U.S. Provisional Application No. 61/095,867 filed Sep. 10, 2008, U.S. Provisional Application No. 61/165,446 filed Mar. 31, 2009, U.S. Provisional Application No. 61/177,113 filed May 11, 2009, and International Application No. PCT/US2009/56172 filed Sep. 8, 2009, each of which is herein incorporated by reference in its entirety.

FIELD OF INVENTION

The present invention generally relates to mixing syringe devices and methods of use thereof.

BACKGROUND OF INVENTION

It is frequently desirable or necessary to mix components of a medical preparation or medicament together immediately prior to use. It is also desirable to mix components in single use batches, to assure consistency in the delivery of the combined components. Frequently, the mixing syringes or other apparatus are also used for storing and maintaining sterility of the components for extended periods prior to the time when they are to be used.

Although many mixing syringes exist, there exists a need for improvement. The present invention provides a simple, efficient multi-chamber mixing syringe device.

SUMMARY OF THE INVENTION

In one aspect of the invention, a mixing syringe device for delivering a medicament or medical composition to a site of interest is provided. The mixing syringe device generally includes a multi-chambered open lumen having at least two longitudinally oriented chambers within the interior of said lumen. Each compartment of the lumen is configured to store a medicament component or medical composition component in its interior. In certain embodiments, each compartment is sealed at one end by a movable stopper mechanism and sealed at the other end by a sealing mechanism capable of temporarily or otherwise opening. By way of example, in certain embodiments, the sealing mechanism is capable of temporarily opening while in other embodiments the sealing mechanism permanently opens, e.g., ruptures or otherwise opens.

In certain embodiments, the mixing syringe device may also include a sectioned plunger having at least two longitudinally oriented extensions corresponding in configuration to the at least two longitudinally oriented chambers of the open lumen. The plunger is generally configured to be reciprocatably disposed in the chambers of the open lumen. In certain embodiments, the plunger is also configured, at least in part, to slidably move the stopper mechanisms to create a pressure differential within the chambers of the open lumen and thereby temporarily or otherwise opening the sealing mechanism upon creation of the pressure differential. By way of example, in certain embodiments, the sealing mechanism is capable of temporarily opening while in other embodiments the sealing mechanism permanently opens, e.g., ruptures or otherwise opens. The plunger may also be configured to provide a means to force the medicament or medical composition from within the mixing syringe device so as to deliver the medicament/medical composition to a site of interest.

In certain embodiments, the multi-chambered open lumen is configured to fit within a syringe barrel, and the mixing syringe device may optionally include a syringe barrel having a hollow interior and an outlet nozzle at a lower end.

These and other aspects of the invention will become apparent to those skilled in the art upon reading the present disclosure.

DETAILED DESCRIPTION OF CERTAIN EMBODIMENTS

The present invention relates generally to a multi-compartment mixing syringe device to deliver multi-component compositions to a site of interest. In certain embodiments, the mixing syringe device may be used to mix and/or reconstitute medicament components or medical compositions prior to administration or delivery to a subject as generally described herein.

The present invention, among other things, provides for improvements in the mixing of medicament components and medical compositions with regard to speed, sterility, consistent proportionality of mixing, cost of manufacture, ease of use; and relative lack of wastage. These and other advantages will become apparent to those skilled in the art upon reading the present disclosure.

Generally, the mixing syringe device may be shaped in any suitable manner for use in a medical setting, such as those known in connection with the use of traditional syringes. For instance, the mixing syringe device will generally include an open cylinder and a cylindrical rod fits within the open cylinder, as generally known in the medical field. However, other overall shapes and dimensions may be utilized as may be recognized by those skilled in the art, and the present invention is not so limited by an open cylinder design. When reference is made to an open cylinder herein, it is recognized that any suitable open lumen and mating plunger may be used. In other embodiments it will be recognized that open lumen configuration may be used wherein mixing of the medicament components may be achieved without the use of the mating plunger via desired sealing stoppers.

Figure 1A:
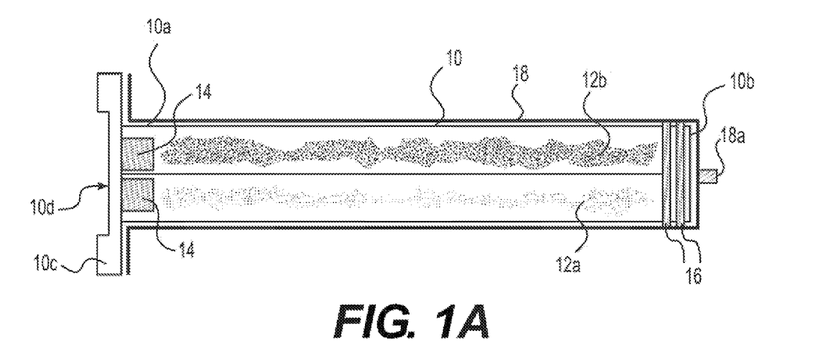
FIG. 1A illustrates a longitudinal section of an embodiment of a multi-chambered open lumen in accordance with certain aspects of the invention.

In accordance with certain embodiments of the present invention, with reference to FIG. 1A, the open lumen 10, e.g., cylinder, may be longitudinally divided into multiple chambers 12a, 12b to store medicament components, e.g., shown in FIG. 1A with two chambers. The number of chambers is generally dependent on the number of medicament components of composition elements to be stored, mixed, delivered, etc. The number of chambers within the open cylinder is limited generally only by the relationship between available cylindrical volume and necessary wall thickness; the relative size of chambers is virtually infinite, as the stoppers can be placed anywhere along the cylinder's length. By way of example, the chamber may be divided in half to form two chambers; divided in thirds to form three chambers; divided in fourths to form four chambers; etc. In addition, the chamber sizes may be equal or vary in size, depending on the required medicament quantity or volume. Medicament quantity or volume may be varied, e.g., via modification of chamber size and/or stopper placement.

Figure 1B:
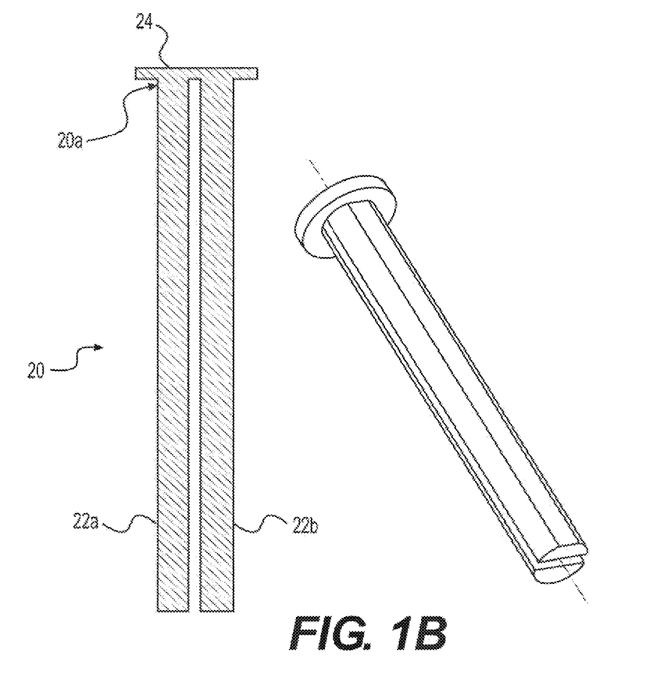
FIG. 1B illustrates a longitudinal section of an embodiment of a sectioned plunger in accordance with certain aspects of the invention.

As illustrated in FIG. 1A, the open lumen may be sized and shaped so as to fit within the hollow interior of the barrel of any standard syringe 18, the syringe 18 including an outlet nozzle 18a. At the 'near' end 10a of the open lumen 10 is a radial flange 10c, which rests against the flange of syringe 18 when the open lumen 10 is fully inserted into the barrel of syringe 18. The external surface of the flange 10c is inset 10d to accept a corresponding plunger (FIG. 1B). At the 'far' end and outer surface 10b of open lumen 10, there is provided a mechanism for creating a seal between the outer surface 10b and the body of syringe 18. Any suitable mechanism may be used, e.g., as shown, one or more rubber or other suitable material rings 16 may be used for creating the seal within the body of syringe 18.

When filled with components of a composition (as illustrated in FIG. 1A), the flanged or 'near' end 10a of open lumen 10 will generally be enclosed in a suitable manner. For example, the near end 10a may be stoppered with rubber (or other suitable material) stoppers 14 which are able to travel down the length of the cylinder while maintaining an effective seal, as a plunger would do as it travels down the chamber of a syringe. The far end 10b will either be covered by a membrane (not shown) that ruptures in a controlled fashion when placed under a pressure differential; and/or, will be seated against a mating seal that is broken when the cylinder is pulled away from the seal. In other embodiments, (not shown) the far end 10b is covered in such as manner so as to allow for temporary opening when placed under a pressure differential. In certain embodiments, during use the separate chambers 12a, 12b of open lumen 10 are filled, partially or fully, with constituents of a medication. Each chamber 12a, 12b of open lumen 10 is sealed at its near end 10a by stoppers 14 that will slide along the chamber's length when pushed by a corresponding plunger (see FIG. 1B).

Turning to FIG. 1B, the present invention provides a plunger corresponding in general dimension to the multi-compartment open lumen's interior so as to mate therewith. In certain embodiments, as illustrated in FIG. 1B, the plunger 20 may be a cylindrical, partially sectioned rod, e.g., shown as a partially bifurcated rod with extensions 22a, 22b in FIG. 1B that correspond to the internal dimensions of chambers 12a, 12b of the open cylinder of FIG. 1A. Sectioned extensions 22a, 22b may be connected at the near end 20a by a disc 24. Generally, sectioned extensions 22a, 22b serve to drive the stoppers 14 from the near end 10a of open lumen 10 to the far end 10b. In certain embodiments, the external dimensions of disc 24 may correspond to the internal dimensions of an inset 10d in the near end flange 10c of open lumen 10. In certain aspects, the plunger's disc 24 may 'click', fasten, or mate into the inset 10d of the flange 10c of open lumen 10 once plunger 20 is fully inserted into the open lumen 10.

Figure 1C:
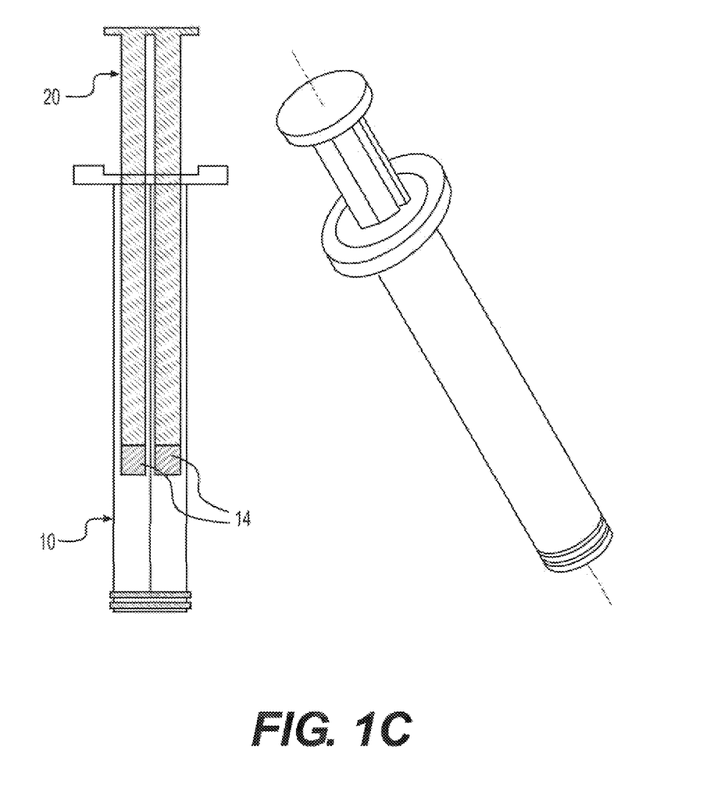
FIG. 1C illustrates a longitudinal section of an embodiment of a multi-chambered mixing syringe device in accordance with certain aspects of the invention.

FIG. 1C shows an exemplary embodiment of a plunger 20 of FIG. 1B conjoined drawing with an open lumen 10 of FIG. 1A, with the rod pushed about three quarters down toward the far end 10c of the open lumen. As shown, plunger 20 is driving stoppers 14 down the cylinder's length.

The design of the seal or membrane on the far end of the open lumen may vary in a suitable manner depending on desired design characteristics, e.g., according to whether it is sealing a liquid or solid or intended to be used with a solid plunger. In certain embodiments, the sealing mechanism may be rupturable or otherwise opened upon application of a pressure differential, or may be temporarily opened via a movable sealing stopper, etc. By way of non-limiting example, in the case of a liquid, a suitable membrane may be used, which may rupture or otherwise open in a controlled manner, such that the liquid is directed in a manner optimum for effective mixing within the syringe barrel, e.g., it may be more effective to have the liquid swirl in the syringe barrel as it is discharged from a chamber of the open lumen. In other embodiments, the sealing mechanism at the far end may be a flap-type, one-way valve particularly suitable for use without the plunger 20 described below.

If desired, the multi-chambered, open lumen 10 may be packaged within a syringe barrel 18 for shipment, etc. Alternatively, the open lumen 10 may be packaged separately and placed within a syringe barrel on site at the time of use. As may be recognized, final configurations may include a cap, tab, and/or other removable safety provision (not shown) to prevent the stoppers 14 being unintentionally displaced, and/or to prevent the cylinder from unintentionally coming out of the syringe barrel, and/or to preserve sterility.

Figure 2A:
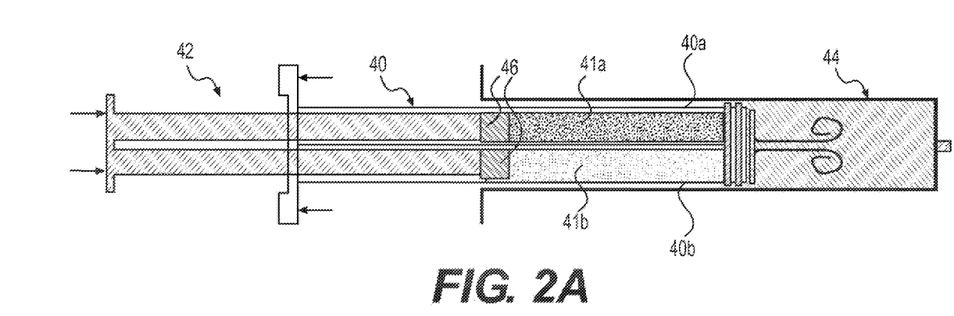
FIG. 2A-2C is an illustration of the use of a multi-chambered mixing syringe device according to an embodiment of the present invention.

FIG. 2A-2C illustrates use of an exemplary embodiment of the invention. As shown with reference to FIG. 2A, the multi-compartment open lumen 40 is shown filled with separate components 41a, 41b of a medicament that are to be mixed prior to discharge from syringe 44. Open lumen's 40 chambers 40a, 40b are stoppered at the near-end with stoppers 46, and each chamber is sealed at the far end with a sealing mechanism such as a membrane as shown at the distal ends of the chambers in FIG. 5 that ruptures or otherwise opens under pressure, or by other means. The filled and sealed multi-compartment chamber is placed within the barrel of syringe 44. In certain embodiments, plunger 42 is used, at least in part, to place pressure on the stoppers 46 as the near-end flange of the multi-chambered open lumen 40 is pulled toward the plunger (indicated by arrows). The pressure differential ruptures or otherwise opens the membrane or other seal (not shown) used to isolate the medicament's components 41a, 41b in the separate chambers 40a, 40b. As the plunger 42 is driven against the stoppers 46, the multi-chambered open lumen 40 rises toward the plunger 42, discharging the medicament's components 41a, 41b into the syringe body. To aid in operation, the far end of the syringe body is preferably stoppered or otherwise closed during the process, by such means as a cap screwed into a Luer lock, a stopcock, or another suitable method (not shown).

Figure 2B:
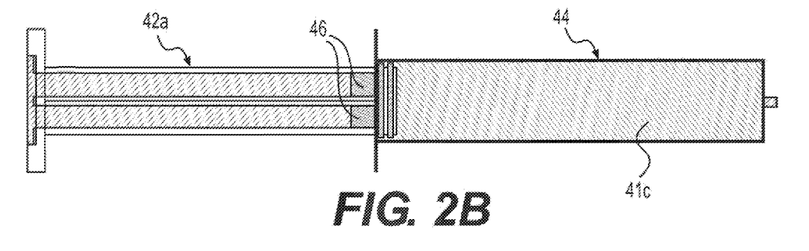
Figure 2C:
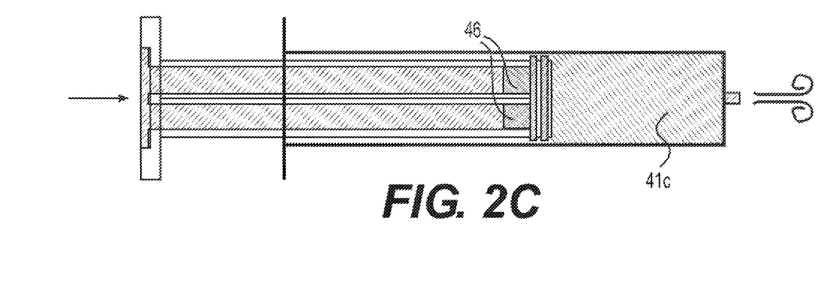

With reference to FIG. 2B, once the plunger 42 is fully inserted into the multi-compartment open lumen 40, the separate components of the medication have been fully mixed in the syringe barrel, the plunger and multi-compartment cylinder have come together to serve as an effective plunger 42a, and can be depressed as a single unit to drive the mixed medicament 41c from the syringe barrel (shown by an arrow in FIG. 2C). Such displacement of the multi-compartment open lumen 40 from the syringe barrel 44 together with the formation of the combined plunger/open lumen as the effective plunger 42a for the final medicament allows for an elegant procedure for delivering the combined medicament.

In other embodiments, the seal at the far end of the open lumen 40 may be configured for use without the plunger. In such configurations, by way of example, the open lumen may be placed within a syringe body and withdrawn from the syringe body in a manner similar to that of a plunger during typical syringe usage. During this embodiment operation, the sealing mechanism opens as the open lumen 40 is withdrawn from the syringe body 44, and the relatively lower pressure in the lumen of the syringe body 44 serves to draw the contents of the open lumen 40 into the syringe body 44. The medicament components of the open lumen compartments are thereby mixed in the syringe body, and by virtue of a one-way valve at the far end of the open lumen 40, stoppers 46 that lodge at the distal end of the open lumen after the medicament components have been withdrawn and/or other means, the open lumen is able to act as syringe plunger to administer the mixed medicament to a subject as needed.

Figure 3:
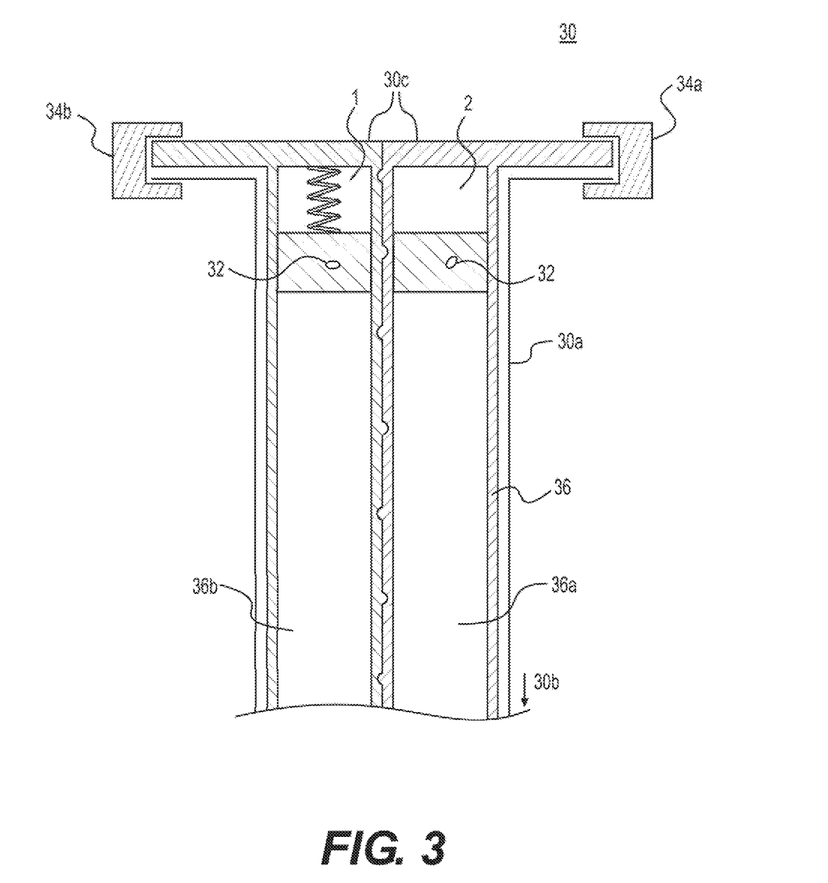
FIG. 3 is an illustration of the use of a multi-chambered mixing syringe device according to another embodiment of the present invention.

As shown with reference to FIG. 3, the movable stoppers 32 may be forced to the far end 30b of the open lumen chambers 36a, 36b by mechanical, pneumatic, or other known automatic mechanism (e.g., springs 1, or means for achieving a pressure differential in the space 2). By way of example, in the embodiment shown, the open lumen 36 is held within the body 30a of a syringe 30 by clips 34a, 34b (or other suitable mechanism), and stoppers 32 are held at the near end 30c of the syringe body 30. On removing clips 34a, 34b, stoppers 32 are driven to the far end 30b of open lumens 36a, 36b, causing medicament components contained therein to mix in the syringe body 30a.

Figure 4:
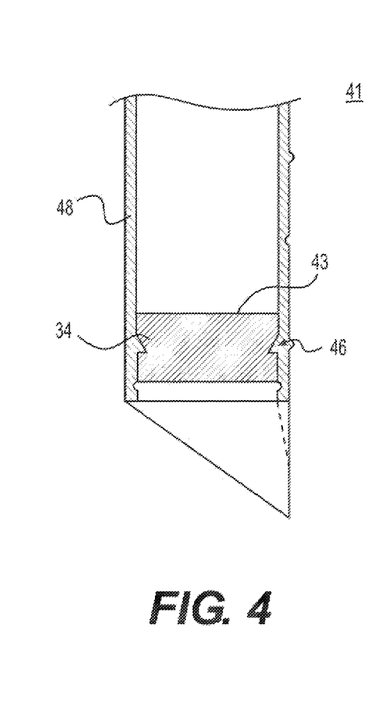
FIG. 4 illustrates an embodiment of a stopper in accordance with certain aspects of the invention.

In other embodiments, the stoppers may be independent of the multi-chambered lumen, may be part of the sectioned rod, etc. In addition, the chambers of the open lumen may optionally include an inward lip at the far end of the chambers to prevent the stoppers from exiting the open lumen, e.g., upon full deployment of the sectioned plunger. In yet another embodiment, as illustrated in FIG. 4, the stoppers 43 may be configured with notches 34 corresponding in size and location to protrusions 46 in the open lumen wall 48 (preferably non-circumferential) so as to "lock" the plunger and/or stopper in place following actuation of the syringe device 41.

Figure 5:
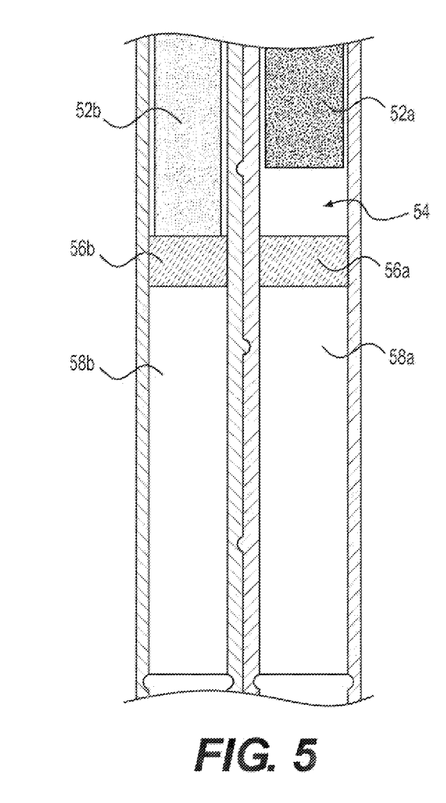
FIG. 5 illustrates an embodiment of a multi-chambered mixing syringe device in accordance with certain aspects of the invention.

In yet other embodiments, as shown in FIG. 5, one of plunger sections 52a, 52b may be configured so as to leave a small space or gap 54 between a plunger section 52a and a stopper section 56a associated with open lumen compartment 58a (filled with a solid medicament component). Without intending to be limited by theory, gap 54 allows liquid medicament component from open lumen compartment 58b to enter open lumen compartment 58a as stopper sections 56a and 56b are actuated into the syringe body so as to better lubricate the solid medicament component and ease the movement of the solid into the syringe body.

The open lumen may be manufactured in any suitable and desired manner as may be known in the art for such purpose. In certain embodiments, the open lumen may be formed from a single, divided compartment and filled in a sterile environment. In other embodiments, the open lumen may be formed from separate compartments, individually filled in sterile environments and assembled as a complete open lumen device as a separate step. In this manner, manufacturing of the medicament constituents may be done separately, allowing for parallel rather than sequential ordering of sterile filling, independent sourcing of the final medicament constituents, minimizing risk of one constituent impacting another during manufacturing/filling, and allowing for the use of distinct materials for each constituent's portion of the open lumen. The separate portions of the open lumen may be secured in any suitable manner, e.g., using snap fittings, medical adhesive, bonding agents, rings 16, etc.

Figure 6A:
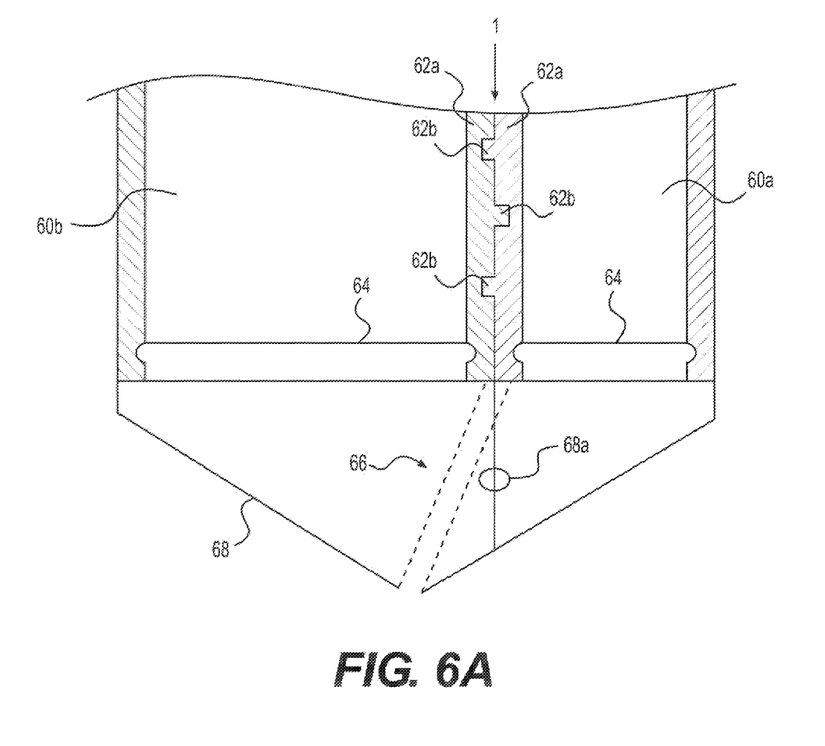
FIGS. 6A-6E illustrate an embodiment of a multi-chambered mixing syringe device in accordance with certain aspects of the invention.

For instance, in one embodiment, as shown in FIGS. 6A-6E, the open lumens may be constructed with corresponding snap-fittings that interact so as to mate the compartments. With reference to FIG. 6A, a longitudinal section of mated open lumen chambers 60a, 60b are shown. As illustrated, the open lumen chambers are of different sizes. However, the invention is not so limited, and any desired configuration could be utilized including additional numbers of chambers, equal sizes of chambers, varied sizes of chambers, etc. Internal features of the individual open lumens are illustrated as follows. Snap-fittings 62b are shown on internal walls 62a. Mating line 68a is shown to illustrate the point of interaction upon connecting open lumen chambers 60a and 60b to form common stopper 68. Each open lumen is illustrated with sealing mechanisms 64 that seal the distal end of each open lumen. Channel 66 is illustrated in dash. As explained herein, channel 66 is occluded prior to actuation of stoppers.

Figure 6B:
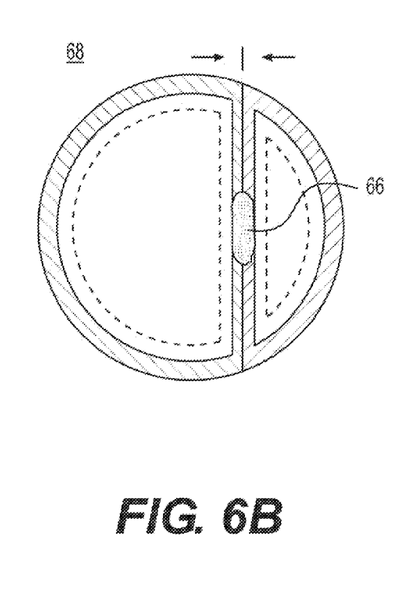
Figure 6C:
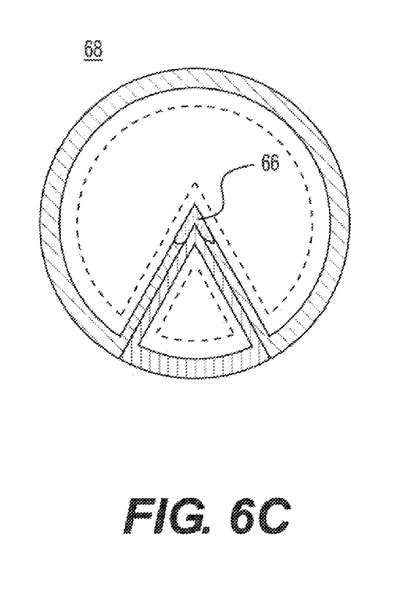

With reference to FIGS. 6B and 6C, surface views of stopper 68 are illustrated showing a snapped together configuration of the stopper from individual open lumen chambers to form one common stopper 68. FIG. 6B illustrates one possible lumen shape configuration, while FIG. 6C illustrates another. Again, the invention is not so limited, and any shape, size, configuration, number, etc. may be utilized as desired. Channel 66 is also illustrated.

Figure 6D:
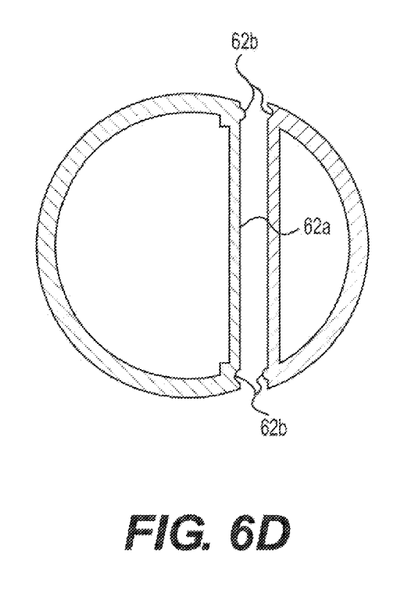
Figure 6E:
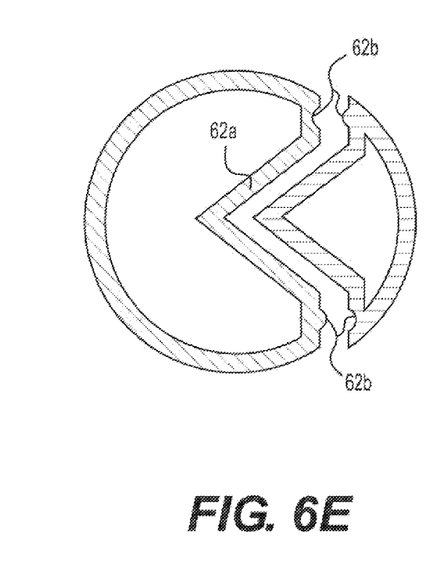

With reference to FIGS. 6D and 6E, cross-sections of open lumen chambers 60a, 60b are illustrated showing snap fittings 62b of individual chamber interior walls 62a. FIG. 6D illustrates one possible lumen shape configuration, while FIG. 6E illustrates another. Again, the invention is not so limited, and any shape, size, configuration, number, etc. may be utilized as desired.

The stoppers, flanges, lips, etc. may be shaped in any suitable and desired manner. In certain embodiments, the elements of the mixing syringe device are sized and shaped to maximize sealing, nesting, grip, ease of use, manufacturing efficiency, etc. Any suitable materials may be used to make the components of the multi-chamber mixing syringe device of the present invention, as recognized by those skilled in the art. In addition, any suitable manufacturing methodology may be used as generally known in the field of syringe and medicament manufacturing. Generally, materials are only limited by compatibility with medicament or medical composition components, generally accepted safety criteria, tolerances with regard to the pressure differentials obtained during use of the device, etc.

By way of non-limiting example, the plunger may be constructed from any suitable solid material, whether metal, plastic, composite, or tempered glass. The open lumen of the cylinder may be constructed from any suitable solid material as well, such as those used in the fabrication of typical syringes (e.g., plastic, polymer, and glass materials). Membranes and stoppers may be formed from suitable synthetic and/or natural rubber materials, as well as various medical grade synthetic plastic films. However, as understood by those skilled in the art, the invention is not so limited.

In another aspect of the invention, a method of providing a medicament or medical composition to a site of interest is provided. In accordance with certain embodiments of the methods of the invention, to mix and/or reconstitute the components of a medicament or medical composition stored with a multi-chambered lumen of the invention, a sectioned plunger is inserted into the near end of the multi-chambered lumen (while the lumen is housed within a syringe barrel), and the near end, e.g., the flange, of the multi-chambered lumen is pulled upward while the sectioned plunger is depressed downward to move the lumen stoppers down the length of the chamber lumen(s). The seal on the far end of the multi-chambered lumen is broken by the pressure differential thus created, and the components of the medicament or medical composition are mixed and/or reconstituted within the barrel of the syringe. At full insertion, the plunger completely fills the lumen, and the plunger/lumen unit now serves as an effective plunger to discharge the mixed/reconstituted medicament or medical composition from the syringe to a site of interest.

Generally, the invention has been described in specific embodiments with some degree of particularity, it is to be understood that this description has been given only by way of example and that numerous changes in the details of construction, fabrication and use, including the combination and arrangement of parts, may be made without departing from the spirit and scope of the invention.

What is claimed:

1. A mixing syringe device for delivering a medicament or medical composition to a site of interest, the mixing syringe device comprising:
    a multi-chambered open lumen having a distal end and a proximal end, and having at least two longitudinally oriented chambers within an interior of said lumen, each of said chambers configured to store a medicament component or medical composition component in an interior;
    movable stopper mechanisms disposed at a first end of each chamber to seal said first end, one or more sealing mechanisms capable of temporarily or otherwise opening at the distal end of the multi-chambered open lumen to thereby enclose said chambers, and a syringe sealing mechanism at the distal end of the multi-chambered open lumen capable of creating a seal between the multi-chambered open lumen and a syringe barrel upon insertion of the multi-chambered open lumen within a hollow interior of the syringe barrel; and
    a syringe barrel having a distal end and a proximal end, and having a hollow interior and an outlet nozzle at said distal end;
    wherein said multi-chambered open lumen is configured to be movably fitted within the hollow interior of said syringe barrel in a sealing arrangement due at least in part to the syringe sealing mechanism, and the one or more sealing mechanisms are configured to temporarily or otherwise open upon creation of a pressure differential within said chambers of said multi-chambered open lumen due at least in part to movable displacement of the distal end of the multi-chambered open lumen toward the proximal end of the syringe barrel such that medicament component or medical composition component stored in the interior of each chamber is released into and mixed in the hollow interior of said syringe barrel to form a medicament or medical composition for delivery to a site of interest upon use.

2. The mixing syringe device of claim 1, further comprising:
    a sectioned plunger having at least two longitudinally oriented extensions corresponding in configuration to the at least two longitudinally oriented chambers of the open lumen and configured to be reciprocatably disposed in said chambers of the open lumen and configured to slidably move said stopper mechanisms to at least partially create said pressure differential within said chambers and thereby temporarily or otherwise open said one or more sealing mechanisms upon creation of said pressure differential.

3. The mixing syringe device of claim 2, wherein the multi-chambered open lumen further comprises a radial flange at a near edge of a first end of the lumen configured to rest against a flange of said syringe barrel when said lumen is fitted within the hollow interior of said syringe barrel.

4. The mixing syringe device of claim 3, wherein the sectioned plunger further comprises a disc at a near edge which is configured to mate with an inset in the radial flange of the multi-chambered open lumen.

5. A method of delivering a medicament or medical composition to a site of interest, the method comprising:
    (a) providing a mixing syringe device of claim 1;
    (b) inserting or ensuring that the multi-chambered open lumen is movably fitted within the syringe barrel;
    (c) inserting or ensuring that a sectioned plunger is fitted into the proximal end of the multi-chambered open lumen, wherein the sectioned plunger has at least two longitudinally oriented extensions corresponding in configuration to the at least two longitudinally oriented chambers of the open lumen configured to be reciprocatably disposed in said chambers of the open lumen and configured to slidably move said stopper mechanisms to at least partially create said pressure differential within said chambers and thereby temporarily or otherwise open said one or more sealing mechanisms upon creation of said pressure differential;
    (d) pulling the proximal end of the multi-chambered open lumen upward and movably displacing the distal end of the multi-chambered open lumen toward the proximal end of the syringe barrel while depressing the sectioned plunger downward to slidably move the stopper mechanisms downward along the length of the chambers to thereby create a pressure differential within said chambers;
    (e) temporarily or otherwise opening the sealing mechanism at the distal end of the multi-chambered open lumen by the pressure differential thus created within each chamber; and
    (f) releasing and mixing/reconstituting the components of the medicament or medical composition within the hollow interior of the syringe barrel for delivery to the site of interest from the syringe barrel.

* * * * *